(12) United States Patent
Takebe et al.

(10) Patent No.: US 7,550,545 B2
(45) Date of Patent: *Jun. 23, 2009

(54) FLUORINATED COMPOUND, AND FLUOROPOLYMER, PROCESS FOR ITS PRODUCTION AND RESIST COMPOSITION CONTAINING IT

(75) Inventors: Yoko Takebe, Yokohama (JP); Isamu Kaneko, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/746,316

(22) Filed: May 9, 2007

(65) Prior Publication Data

US 2007/0207409 A1  Sep. 6, 2007

Related U.S. Application Data

(60) Division of application No. 11/336,943, filed on Jan. 23, 2006, which is a continuation of application No. PCT/JP2004/010856, filed on Jul. 29, 2004.

(30) Foreign Application Priority Data

Jul. 31, 2003  (JP)  ............................. 2003-284156
Mar. 25, 2004 (JP)  ............................. 2004-088337

(51) Int. Cl.
    *C08F 136/16* (2006.01)
(52) U.S. Cl. ..................... 526/252; 430/270.1; 430/914; 430/945; 526/242
(58) Field of Classification Search ................. 526/252, 526/242; 430/270.1, 914, 945
    See application file for complete search history.

(56) References Cited

U.S. PATENT DOCUMENTS

| 6,310,142 | B1 * | 10/2001 | Apostolo et al. ............ 525/200 |
| 6,670,511 | B2 * | 12/2003 | Kashiwagi et al. .......... 568/683 |
| 6,815,146 | B2   | 11/2004 | Okada et al. |
| 6,818,258 | B2   | 11/2004 | Kaneko et al. |
| 6,858,692 | B2 * | 2/2005  | Kaneko et al. ............ 526/252 |
| 7,015,366 | B2   | 3/2006  | Kodama et al. |
| 2005/0234206 | A1 * | 10/2005 | Takebe et al. ............ 526/245 |
| 2006/0004164 | A1 * | 1/2006  | Kodama et al. ............ 526/249 |
| 2006/0122348 | A1 * | 6/2006  | Takebe et al. ............ 526/252 |
| 2006/0135663 | A1 * | 6/2006  | Takebe et al. ............ 524/157 |
| 2006/0188816 | A1   | 8/2006  | Takebe et al. |
| 2007/0083021 | A1   | 4/2007  | Eda et al. |
| 2007/0154844 | A1 * | 7/2007  | Takebe et al. ............ 430/311 |
| 2007/0207409 | A1 * | 9/2007  | Takebe et al. ........... 430/270.1 |

FOREIGN PATENT DOCUMENTS

| EP | 1 365 290 | 11/2003 |
| EP | 1365290 A1 | 11/2003 |
| EP | 1 367 071 | 12/2003 |
| EP | 1367071 A1 | 12/2003 |
| JP | 04-189880 | 7/1992 |
| JP | 04/226177 | 8/1992 |
| JP | 06/220232 | 8/1994 |
| WO | 00/17712 | 3/2000 |
| WO | 01/37044 | 5/2001 |
| WO | 01/63362 | 8/2001 |
| WO | 02/064648 | 8/2002 |
| WO | 02/065212 | 8/2002 |
| WO | WO-02/064648 | 8/2002 |
| WO | WO-02/064648 A1 * | 8/2002 |
| WO | WO-02/065212 | 8/2002 |

OTHER PUBLICATIONS

U.S. Appl. No. 11/746,316, filed May 9, 2007, Takebe, et al.
U.S. Appl. No. 11/626,913, filed Jan. 25, 2007, Takebe, et al.

* cited by examiner

*Primary Examiner*—Peter D. Mulcahy
*Assistant Examiner*—Henry Hu
(74) *Attorney, Agent, or Firm*—Oblon, Spivak, McClelland, Maier & Neustadt, P.C.

(57) ABSTRACT

To provide a fluoropolymer having functional groups and having high transparency in a wide wavelength region, and a resist composition comprising the fluoropolymer.

A fluoropolymer (A) having monomer units formed by polymerization of a fluorinated diene represented by the following formula (1):

$$CF_2=CFCH_2CH-Q-CH_2CH=CH^2 \qquad (1)$$

wherein Q is $(CH_2)_aC(CF_3)_2OR^4$ (wherein a is an integer of from 0 to 3, $R^4$ is an alkyl group or a fluorinated alkyl group having at most 20 carbon atoms which may have an etheric oxygen atom, an alkoxycarbonyl group having at most 6 carbon atoms, or $CH_2R^5$ (wherein $R^5$ is an alkoxycarbonyl group having at most 6 carbon atoms)), or $(CH_2)_dCOOR^6$ (wherein d is 0 or 1, and $R^6$ is a hydrogen atom, or an alkyl group or a fluorinated alkyl group having at most 20 carbon atoms), a process for its production and a resist composition having the fluoropolymer (A) as a base.

9 Claims, No Drawings

FLUORINATED COMPOUND, AND FLUOROPOLYMER, PROCESS FOR ITS PRODUCTION AND RESIST COMPOSITION CONTAINING IT

TECHNICAL FIELD

The present invention relates to a novel fluorinated compound, a fluoropolymer and a process for its production, and a resist composition.

BACKGROUND ART

As fluoropolymers having functional groups, functional group-containing fluoropolymers are known which are used for fluorinated ion exchange membranes, curable fluorinated resin coating materials, etc. However, they are all basically straight chained polymers, and they are obtainable by copolymerization of a fluoroolefin represented by tetrafluoroethylene with a monomer having a functional group.

Further, a polymer containing functional groups and having a fluorinated alicyclic structure in its main chain, is also known. As a method for introducing functional groups to the polymer having a fluorinated alicyclic structure in its main chain, a method of utilizing terminal groups of a polymer obtained by polymerization, a method of subjecting a polymer to high temperature treatment to oxidize and decompose side chains or terminals of the polymer to form functional groups, or a method of copolymerizing a monomer having a functional group, if necessary, by adding treatment such as hydrolysis to introduce functional groups, is, for example, known (see Patent Documents 1, 2, 3 and 4).

The above-mentioned methods are available as methods for introducing functional groups to a polymer having a fluorinated alicyclic structure in its main chain. However, the method for introducing functional groups by treating the terminal groups of the polymer, has a drawback that the functional group concentration is low, and no adequate characteristics of the functional groups can be obtained. Whereas, by the method for introducing functional groups by copolymerizing a monomer having a functional group, there will be a problem such that if the functional group concentration is increased, the mechanical properties tend to decrease due to a decrease of the glass transition temperature (Tg).

Patent Document 1: JP-A-4-189880
Patent Document 2: JP-A-4-226177
Patent Document 3: JP-A-6-220232
Patent Document 4: WO02/064648

DISCLOSURE OF THE INVENTION

Problems that the Invention is to Solve

The present invention provides a fluorinated compound having high concentration of functional groups and adequate characteristics of the functional groups and having high transparency in a wide wavelength region, a fluoropolymer and a process for its production. Further, the present invention provides a resist composition which can form a chemical amplification type resist excellent particularly in transparency for far ultraviolet rays such as KrF or ArF excimer laser or vacuum ultraviolet rays such as $F_2$ excimer laser and dry etching characteristics, and a resist pattern excellent in sensitivity, resolution, dissolution velocity, flatness and the like.

Means of Solving the Problems

The present invention is to solve the above problems, and has the following gists.

(1) The present invention provides a fluoropolymer (A) having monomer units formed by cyclopolymerization of a fluorinated diene containing functional groups represented by the following formula (1):

wherein each of $R^1$ and $R^2$ which are independent of each other, is a hydrogen atom or an alkyl group having at most 12 carbon atoms, Q is $(CH_2)_aC(CF_3)_b(R^3)_cOR^4$ (wherein a is an integer of from 0 to 3, b and c are integers of from 0 to 2 satisfying b+c=2, $R^3$ is a hydrogen atom or a methyl group, $R^4$ is an alkyl group or a fluorinated alkyl group having at most 20 carbon atoms which may have an etheric oxygen atom, an alkoxycarbonyl group having at most 6 carbon atoms, or $CH_2R^5$ (wherein $R^5$ is an alkoxycarbonyl group having at most 6 carbon atoms)), or $(CH_2)_dCOOR^6$ (wherein d is 0 or 1, and $R^6$ is a hydrogen atom, or an alkyl group or a fluorinated alkyl group having at most 20 carbon atoms).

(2) The present invention provides a method for producing a fluoropolymer (A), characterized by cyclopolymerization of a fluorinated diene containing functional groups represented by the above formula (1).

(3) The present invention provides a fluorinated diene represented by the following formula (2) or (3):

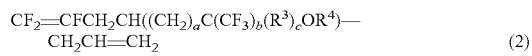

wherein a is an integer of from 0 to 3, b and c are integers of from 0 to 2 satisfying b+c=2, $R^3$ is a hydrogen atom or a methyl group, $R^4$ is an alkyl group or a fluorinated alkyl group having at most 20 carbon atoms which may have an etheric oxygen atom, an alkoxycarbonyl group having at most 6 carbon atoms or $CH_2R^5$ (wherein $R^5$ is an alkoxycarbonyl group having at most 6 carbon atoms),

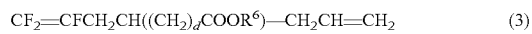

wherein d is 0 or 1, and $R^6$ is a hydrogen atom, or an alkyl group or a fluorinated alkyl group having at most 20 carbon atoms.

(4) The present invention provides a resist composition characterized by comprising the above fluoropolymer (A), an acid-generating compound (B) which generates an acid under irradiation with light, and an organic solvent (C).

Effect of the Invention

According to the present invention, it is possible to produce a fluoropolymer having an alicyclic structure in its main chain and having functional groups in its side chains. The fluoropolymer (A) obtained by the present invention has high chemical stability and heat resistance. Yet, functional groups are introduced in the side chains, whereby it is possible to exhibit sufficient characteristics of functional groups without bringing about a decrease of Tg, which used to be difficult to accomplish with conventional fluoropolymers. Further, such a fluoropolymer (A) has high transparency in a wide wavelength region. The resist composition of the present invention can be used as a chemical amplification type resist excellent particularly in transparency for far ultraviolet rays such as

BEST MODE FOR CARRYING OUT THE INVENTION

By the present invention, a polymer having monomer units formed by cyclopolymerization of a fluorinated diene represented by the following formula (1) (hereinafter referred to as the fluorinated diene (1), the same applies hereinafter), and a process for its production can be provided:

$$CF_2=CFCH_2CHQ\text{-}CH_2CR^1=CHR^2 \quad (1)$$

wherein each of $R^1$ and $R^2$ which are independent of each other, is a hydrogen atom or an alkyl group having at most 12 carbon atoms. The alkyl group having at most 12 carbon atoms may have not only a straight or branched aliphatic hydrocarbon but also an alicyclic hydrocarbon group. The alicyclic hydrocarbon group is preferably a hydrocarbon group having at least one cyclic structure, and it includes, for example, the following monocyclic saturated hydrocarbon groups, such as a cyclobutyl group, a cycloheptyl group and a cyclohexyl group, bicyclic saturated hydrocarbon groups such as a 4-cyclohexylcyclohexyl group, polycyclic saturated hydrocarbon groups such as 1-decahydronaphthyl group and 2-decahydronaphthyl group, crosslinked cyclic saturated hydrocarbon groups such as a 1-norbornyl group and a 1-adamantyl group, and spirohydrocarbon groups such as a spiro[3,4]octyl group:

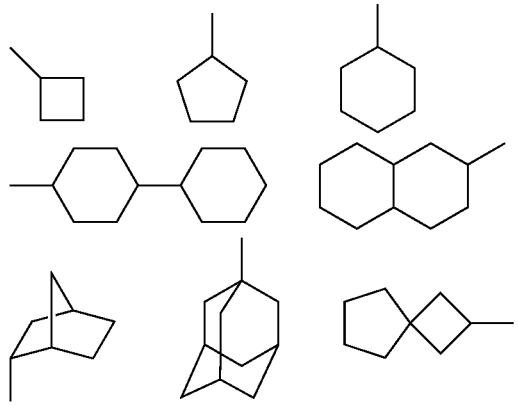

Each of the above $R^1$ and $R^2$ is preferably a hydrogen atom, a methyl group or an alicyclic hydrocarbon groups having at most 6 carbon atoms, particularly preferably a hydrogen atom or a methyl group. Both $R^1$ and $R^2$ are most preferably hydrogen atoms.

Q is $(CH_2)_aC(CF_3)_b(R^3)_cOR^4$ (wherein a is an integer of from 0 to 3, and is preferably 0 or 1. b and c are integers of from 0 to 2 satisfying b+c=2, $R^3$ is a hydrogen atom or a methyl group, $R^4$ is an alkyl group or a fluorinated alkyl group having at most 20 carbon atoms which may have an etheric oxygen atom, an alkoxycarbonyl group having at most 6 carbon atoms, or $CH_2R^5$ (wherein $R^5$ is an alkoxycarbonyl group having at most 6 carbon atoms)), or $(CH_2)_dCOOR^6$ (wherein d is 0 or 1, and $R^6$ is a hydrogen atom, or an alkyl group or a fluorinated alkyl group having at most 20 carbon atoms).

The alkyl group or the fluorinated alkyl group having at most 20 carbon atoms which may have an etheric oxygen atom, may have not only a straight or branched aliphatic hydrocarbon group but also an alicyclic hydrocarbon group. As the alicyclic hydrocarbon group, the same group as mentioned above may be used, or may have an etheric oxygen atom in its cyclic structure. The specific examples may be a methyl group, a trifluoromethyl group, $t\text{-}C_4H_9$, $CH_2OCH_3$, $CH_2OC_2H_5$, $CH_2OCH_2CF_3$, a 2-tetrahydropyranyl group and the following groups (in order to make clear their bonding position, they are shown in the form of $—OR^4$).

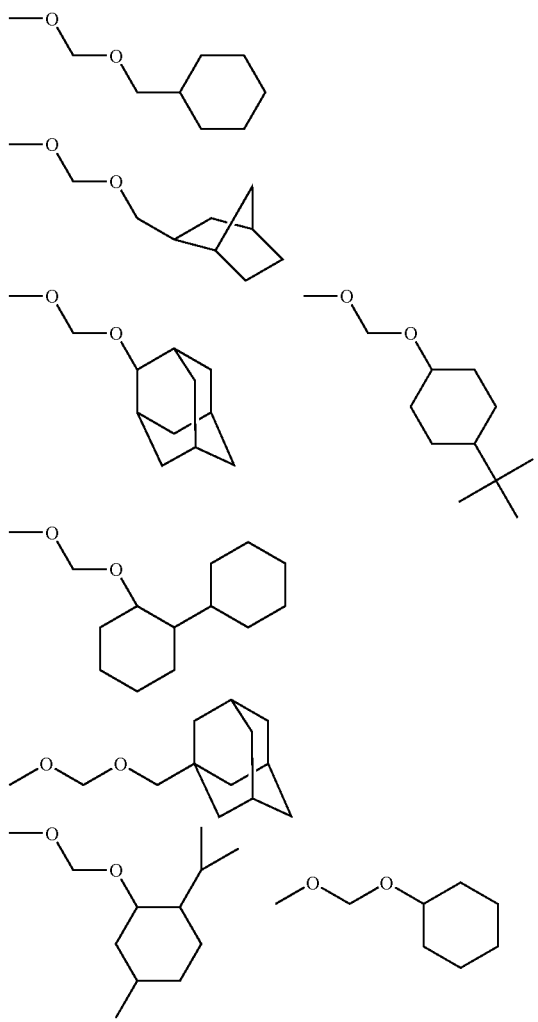

The alkoxycarbonyl group having at most 6 carbon atoms and $CH_2R^5$ may be represented by $COOR^7$ and $CH_2COOR^7$ ($R^7$ is an alkyl group having at most 5 carbon atoms), respectively, and as specific examples, $COO(t\text{-}C_4H_9)$ and $CH_2COO(t\text{-}C_4H_9)$ may be mentioned, respectively.

The alkyl group having at most 20 carbon atoms or the fluorinated alkyl group in $R^6$ may have an alicyclic hydrocarbon atom, and preferably has at most 12 carbon atoms. As the alicyclic hydrocarbon group, the same group as mentioned above may be used, and the following groups may specifically be mentioned (in order to make clear their bonding position, they are shown in the form of $—OR^6$).

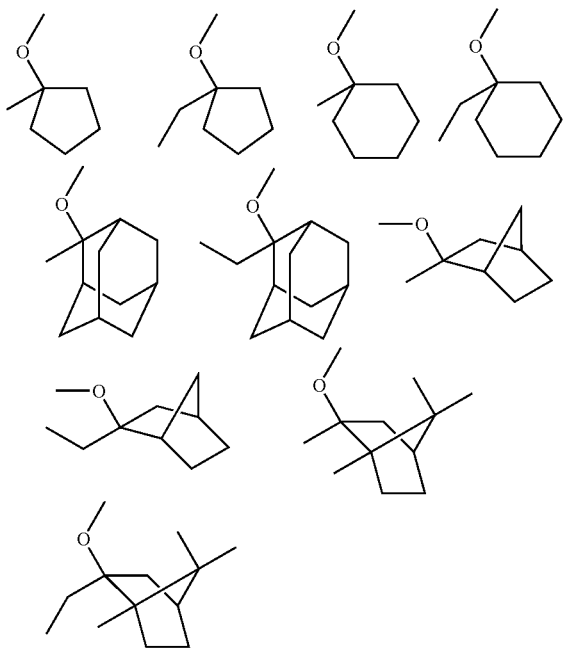

$R^6$ is preferably a hydrogen atom or an alkyl group having at most 4 carbon atoms, particularly preferably a hydrogen atom or a t-butyl group.

As the fluoropolymer (A) of the present invention, it is preferred that in the above formula (1), each of $R^1$ and $R^2$ which are independent of each other, is a hydrogen atom, a methyl group or an alicyclic hydrocarbon group having at most 6 carbon atoms, and Q is $(CH_2)_aC(CF_3)_b(R^3)_cOR^4$ (wherein a is an integer of from 0 to 3, b and c are integers of from 0 to 2 satisfying b+c=2, $R^3$ is a hydrogen atom or a methyl group, $R^4$ is an alkyl group having at most 5 carbon atoms which may have an etheric oxygen atom, an alkoxycarbonyl group having at most 6 carbon atoms, or $CH_2R^5$ (wherein $R^5$ is an alkoxycarbonyl group having at most 6 carbon atoms)), or $(CH_2)_dCOOR^6$ (wherein d is 0 or 1, and $R^6$ is a hydrogen atom, or an alkyl group or a fluorinated alkyl group having at most 20 carbon atoms). Further, in the above, $R^6$ is more preferably a hydrogen atom or an alkyl group having at most 5 carbon atoms.

Further, the fluoropolymer (A) of the present invention is particularly preferably a fluoropolymer having monomer units formed by cyclopolymerization of a fluorinated diene represented by the following formula (2) or (3). a, b, c, d, $R^3$, $R^4$ and $R^6$ are as mentioned above.

$$CF_2=CFCH_2CH((CH_2)_aC(CF_3)_b(R^3)_cOR^4)-CH_2CH=CH_2 \qquad (2)$$

$$CF_2=CFCH_2CH((CH_2)_dCOOR^6)-CH_2CH=CH_2 \qquad (3)$$

Such a fluorinated diene (1) can be polymerized under a relatively mild condition, whereby a cyclized polymer having ether groups, ester groups or carboxylic acid groups in side chains of the cyclic structure, can be obtained.

By the cyclopolymerization of the fluorinated diene (1), the following monomer units (a) to (c) are considered to be formed, and from the results of the spectroscopic analyses, etc., the fluoropolymer (A) is considered to be a polymer having a structure comprising at least one type of monomer units selected from the group consisting of monomer units (a), monomer units (b) and monomer units (c). Further, the main chain of the fluoropolymer (A) is meant for a carbon chain constituted by carbon atoms which constitute polymerizable unsaturated bonds (in the case of the fluorinated diene (1), the four carbon atoms which constitute polymerizable unsaturated double bonds).

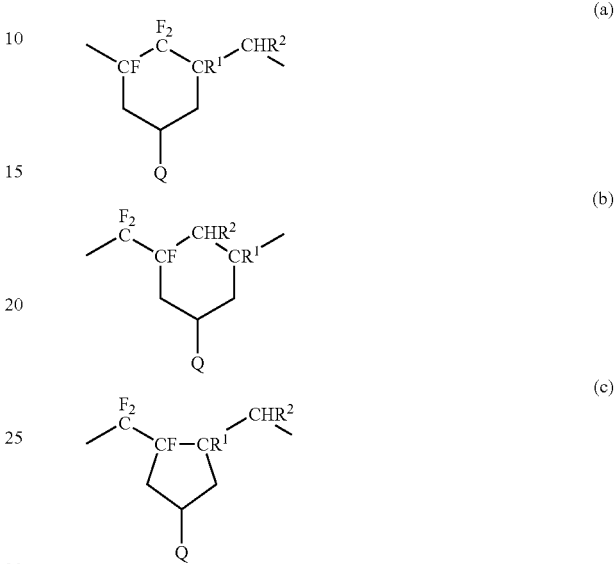

The fluoropolymer (A) contains monomer units formed by cyclopolymerization of the fluorinated diene (1), as essential components, but may further contain monomer units derived from other radical polymerizable monomers (hereinafter referred to as other monomers) within a range not to impair the characteristics. The proportion of such other monomer units is preferably at most 50 mol %, particularly preferably at most 15 mol %.

Such other monomers may, for example, be an α-olefin such as ethylene, propylene or isobutylene, a fluorinated olefin such as tetrafluoroethylene or hexafluoropropylene, a fluorinated cyclic monomer such as perfluoro(2,2-dimethyl-1,3-dioxol), a cyclopolymerizable perfluorodiene or hydrofluorodiene, such as perfluoro(butenyl vinyl ether), an acryl ester such as methyl acrylate or ethyl methacrylate, a vinyl ester such as vinyl acetate, vinyl benzoate or vinyl adamantate, a vinyl ether such as ethyl vinyl ether or cyclohexyl vinyl ether, a cyclic olefin such as cyclohexene, norbornene or norbornadiene, maleic anhydride, or vinyl chloride.

The fluoropolymer (A) of the present invention can be obtained by homopolymerizing the fluorinated diene (1) or copolymerizing it with the copolymerizable other monomer in the presence of a polymerization initiating source. The polymerization initiating source is not particularly limited so long as it is capable of letting the polymerization reaction proceed radically, and it may, for example, be a radical-generating agent, light or ionizing radiation. A radical-generating agent is particularly preferred, and it may, for example, be a peroxide, an azo compound or a persulfate. Among them, the following peroxides are preferred.

$C_6H_5-C(O)O-OC(O)-C_6H_5$
$C_6F_5-C(O)O-OC(O)-C_6F_5$
$C_3F_7-C(O)O-OC(O)-C_3F_7$
$(CH_3)_3C-C(O)O-OC(O)-C(CH_3)_3$
$(CH_3)_2CH-C(O)O-OC(O)-CH(CH_3)_2$ (CH₃)₃C—C₆H₁₀—C(O)O—OC(O)—C₆H₁₀—C(CH₃)₃
(CH₃)₃C—O—C(O)O—OC(O)—O—C(CH₃)₃,
(CH₃)₂CH—O—C(O)O—OC(O)—O—CH(CH₃)₂,
(CH₃)₃C—C₆H₁₀—O—C(O)O—OC(O)—O—C₆H₁₀—C(CH₃)₃.

Here, $C_6H_5$ represents a phenyl group, $C_6F_5$ a pentafluorophenyl group and $C_6H_{10}$ a cyclohexylene group.

The polymerization method is also not particularly limited, and it may, for example, be so-called bulk polymerization wherein a monomer is subjected to polymerization as it is, solution polymerization which is carried out in a fluorohydrocarbon, a chlorohydrocarbon, a fluorochlorohydrocarbon, an alcohol, a hydrocarbon or other organic solvent, in which the fluorinated diene (1) and the other monomer can be dissolved or dispersed, suspension polymerization which is carried out in an aqueous medium in the absence or presence of a suitable organic solvent, or emulsion polymerization which is carried out in an aqueous medium in the presence of an emulsifier.

The polymerization temperature and pressure are also not particularly limited, but it is preferred to properly set them taking into consideration various factors such as the boiling point of the monomer, the heating source, removal of the polymerization heat, etc. For example, suitable temperature setting can be carried out between 0° C. to 200° C., and practically suitable temperature setting can be carried out within a range of from room temperature to 100° C. Further, the polymerization pressure may be a reduced pressure or an elevated pressure, and practically, the polymerization can properly be carried out within a range of from normal pressure to about 100 atom, preferably from normal pressure to 10 atom.

Further, the present invention provides a fluorinated diene represented by the following formula (2) or (3) is which can form suitable polymers among the fluoropolymer (A):

$$CF_2=CFCH_2CH((CH_2)_aC(CF_3)_b(R^3)_cOR^4)—CH_2CH=CH_2 \quad (2)$$

wherein a, b, c are as defined above, and it is preferred that b is 1 and c is 1, or b is 2 and c is 0. $R^3$ and $R^4$ are as defined above.

$$CF_2=CFCH_2CH((CH_2)_dCOOR^6)—CH_2CH=CH_2 \quad (3)$$

wherein d and $R^6$ are as defined above.

The following compounds may be mentioned as specific examples of the fluorinated diene (2) and the fluorinated diene (3) of the present invention, but the present invention is not limited thereto.

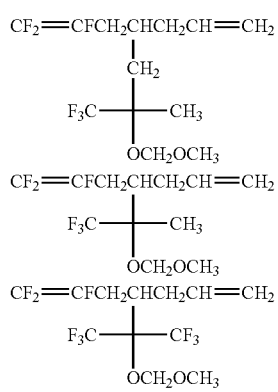

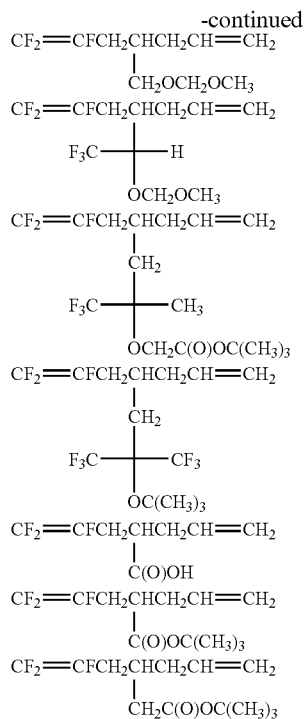

Further, the present invention provides a resist composition comprising a fluoropolymer (A), an acid-generating compound (B) which generates an acid under irradiation with light and an organic solvent (C).

The acid-generating compound (B) which generates an acid under irradiation with light of the present invention generates an acid under irradiation with light. By the acid thus generated, a blocked acidic group which exists in the fluoropolymer (A), is cleaved (deblocked). As a result, the exposed portions of the resist film will become readily soluble by an alkali developer, whereby a positive resist pattern will be formed by the alkali developer. As such an acid-generating compound (B) which generates an acid under irradiation with light, it is possible to employ an acid-generating compound which is commonly used for a chemical amplification type resist material. Namely, an onium salt, a halogenated compound, a diazoketone compound, a sulfone compound or a sulfonic acid compound may, for example, be mentioned. The following compounds may be mentioned as examples of such an acid-generating compound (B).

The onium salt may, for example, be an iodonium salt, a sulfonium salt, a phosphonium salt, a diazonium salt or a pyridinium salt. Specific examples of a preferred onium salt include diphenyliodonium triflate, diphenyliodoniumpyrene sulfonate, diphenyliodoniumdodecylbenzene sulfonate, bis(4-tert-butylphenyl)iodonium triflate, bis(4-tert-butylphenyl)iodonium dodecylbenzene sulfonate, triphenylsulfonium triflate, triphenylsulfonium nonanate, triphenylsulfoniumperfluorooctane sulfonate, triphenylsulfonium hexafluoroantimonate, 1-(naphthylacetomethyl)thiolanium triflate, cyclohexylmethyl(2-oxocyclohexyl)sulfonium triflate, dicyclohexyl(2-oxocyclohexyl)sulfonium triflate, dimethyl(4-hydroxynaphthyl)sulfonium tosylate, dimethyl(4-hydroxynaphthyl)sulfonium dodecylbenzene sulfonate, dimethyl(4-hydroxynaphthyl)sulfonium naphthalene sulfonate, triphenylsulfonium camphor sulfonate or (4-hydroxyphenyl)benzylmethylsulfonium toluene sulfonate.

The halogenated compound may, for example, be a haloalkyl group-containing hydrocarbon compound or a haloalkyl group-containing heterocyclic compound. Specifically, it may, for example, be a (trichloromethyl)-s-triazine derivative such as phenyl-bis(trichloromethyl)-s-triazine, methoxyphenyl-bis(trichloromethyl)-s-triazine or naphthyl-bis(trichloromethyl)-s-triazine, or 1,1-bis(4-chlorophenyl)-2,2,2-trichloroethane.

The sulfone compound may, for example, be β-ketosulfone, β-sulfonylsulfone or an α-diazo compound of such a compound. Specifically, it may, for example, be 4-trisphenacylsulfone, mesitylphenacylsulfone or bis(phenylsulfonyl) methane. The sulfonic acid compound may, for example, be an alkylsulfonic acid ester, an alkylsulfonic acid imide, a haloalkylsulfonic acid ester, an arylsulfonic acid ester or an iminosulfonate. Specifically, it may, for example, be benzoine tosylate or 1,8-naphthalene dicarboxylic acid imide triflate. In the present invention, such acid-generating compounds (B) may be used alone or in combination as a mixture of two or more of them.

The organic solvent (C) of the present invention is not particularly limited so long as it is capable of dissolving both components (A) and (B). It may, for example, be an alcohol such as methyl alcohol or ethyl alcohol, a ketone such as acetone, methylisobutyl ketone or cyclohexanone, an acetate such as ethyl acetate or butyl acetate, an aromatic hydrocarbon such as toluene or xylene, a glycol monoalkyl ether such as propylene glycol monomethyl ether or propylene glycol monoethyl ether, or a glycol monoalkyl ether ester such as propylene glycol monomethyl ether acetate or carbitol acetate.

The proportions of the respective components in the resist composition of the present invention are usually such that the acid-generating compound (B) is from 0.1 to 20 parts by mass and the organic solvent (C) is from 50 to 2,000 parts by mass, per 100 parts by mass of the fluoropolymer (A). Preferably, the acid-generating compound (B) is from 0.1 to 10 parts by mass and the organic solvent (C) is from 100 to 1,000 parts by mass, per 100 parts by mass of the fluoropolymer (A).

If the amount of the acid-generating compound (B) is at least 0.1 part by mass, a sufficient sensitivity and developability can be provided, and if it is at most 10 parts by mass, a sufficient transparency to radiation is retained, whereby a more accurate resist pattern can be obtained.

In the resist composition of the present invention, an acid-cleavable additive to improve the pattern contrast, a surfactant to improve the coating property, a nitrogen-containing basic compound to adjust the acid-generating pattern, an adhesion-assisting agent to improve the adhesion to a substrate or a storage stabilizer to enhance the storage stability of the composition, may be optionally incorporated. Further, the resist composition of the present invention is preferably employed in such a manner that the respective components are uniformly mixed, followed by filtration by means of a filter of from 0.1 to 2 μm.

The resist composition of the present invention is coated on a substrate such as a silicon wafer, followed by drying to form a resist film. As the coating method, spin coating, cast coating or roll coating may, for example, be employed. The formed resist film will be irradiated with light through a mask having a pattern drawn thereon, followed by development treatment to form the pattern.

The light beams for the irradiation may, for example, be ultraviolet rays such as g-line having a wavelength of 436 nm or i-line having a wavelength of 365 nm, or far ultraviolet rays or vacuum ultraviolet rays, such as KrF excimer laser having a wavelength of 248 nm, ArF excimer laser having a wavelength of 193 nm or $F_2$ excimer laser having a wavelength of 157 nm. The resist composition of the present invention is a resist composition useful particularly for an application where ultraviolet rays having a wavelength of at most 250 nm, especially ultraviolet rays having a wavelength of at most 200 nm (such as ArF excimer laser or $F_2$ excimer laser), are used as the light source.

As the development treatment solution, various alkali aqueous solutions are employed. As such an alkali material, sodium hydroxide, potassium hydroxide, ammonium hydroxide, tetramethylammonium hydroxide or triethylamine may, for example, be mentioned.

EXAMPLES

Now, the present invention will be described in detail with reference to Examples, but it should be understood that the present invention is by no means restricted thereto.

Abbreviations used in the following Examples are as follows.

THF: tetrahydrofuran, AIBN: azobisisobutyronitrile, BPO: benzoyl peroxide, PSt: polystyrene, R225: dichloropentafluoropropane (solvent), IPP: diisopropylperoxydicarbonate, Cy: cyclohexyl group and AdM: 2-methyladamantan-2-yl group (as follows).

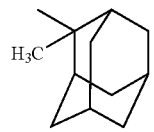

AdM

Example 1

Preparation of $CF_2\!\!=\!\!CFCH_2CH(CH_2C(CF_3)_2OCH_2OCH_3)CH_2CH\!\!=\!\!CH_2$ Into a 200 mL glass reactor, 118 g of $CF_2ClCFClI$ and 1.1 g of AIBN were put and heated to 75° C. 75.8 g of $CH_2\!\!=\!\!CHCH_2C(CF_3)_2OCH_2OCH_3$ was dropwise added thereto over a period of 1 hour. After completion of the dropwise addition, the mixture was stirred at 75° C. for 7 hours, and distilled under reduced pressure to obtain 144 g of $CF_2ClCFClCH_2CHI(CH_2C(CF_3)_2OCH_2OCH_3)$ (80-85° C./0.16 kPa).

Into a 2 L glass reactor, 144 g of the above prepared $CF_2ClCFClCH_2CHI(CH_2C(CF_3)_2OCH_2OCH_3)$ and 550 mL of dehydrated THF were put and cooled to −75° C. 220 mL of a 2M-THF solution of $CH_2\!\!=\!\!CHCH_2MgCl$ was dropwise added thereto over a period of 2 hours.

After stirring at −75° C. for 3 hours, 400 mL of an aqueous saturated ammonium chloride solution was added thereto, and the temperature was raised to room temperature. The reaction solution was subjected to liquid separation, and the organic layer was concentrated by an evaporator and then distilled under reduced pressure to obtain 66.3 g of $CF_2ClCFClCH_2CH(CH_2C(CF_3)_2OCH_2OCH_3)$ $CH_2CH\!\!=\!\!CH_2$ (54-56° C./0.08 kPa). Into a 200 mL glass reactor, 30 g of zinc and 100 g of water were put and heated to 85° C. Then, 66.3 g of the above prepared CF$_2$ClCFClCH$_2$CH(CH$_2$C(CF$_3$)$_2$OCH$_2$OCH$_3$)CH$_2$CH=CH$_2$ was dropwise added thereto, followed by stirring for 24 hours. The reaction solution was filtrated and subjected to liquid separation, and then distilled under reduced pressure to obtain 23.6 g of CF$_2$=CFCH$_2$CH(CH$_2$C(CF$_3$)$_2$OCH$_2$OCH$_3$)CH$_2$CH=CH$_2$ (54-56° C./0.5 kPa).

NMR spectra $^1$H-NMR (399.8 MHz, solvent: CDCl$_3$, standard: tetramethylsilane) δ (ppm): 1.92(m, 2H), 2.33(m, 5H), 3.44(s, 3H), 3.74(br, 1H), 4.95(m, 2H), 5.12(m, 2H), 5.75(m, 1H).

$^{19}$F-NMR (376.2 MHz, solvent: CDCl$_3$, standard: CFCl$_3$) δ (ppm): −77.3 (m, 3F), −77.8 (m, 3F), −92.9 (m, 1F), −104.2 (dd, J=33.24, 85.97 Hz, 1F), −123.5 (dd, J=85.97, 113.9 Hz, 1F), −171.9 (m, 1F).

Example 2

Preparation of CF$_2$=CFCH$_2$CH(CH$_2$C(CF$_3$)$_2$OCH$_2$OCH$_3$)CH$_2$C(Cy)=CH$_2$ CF$_2$=CFCH$_2$CH(CH$_2$C(CF$_3$)$_2$OCH$_2$OCH$_3$)CH$_2$C(Cy)=CH$_2$ can be obtained by carrying out the preparation in the same manner as in Example 1 except that in Example 1, 220 mL of a 2M-THF solution of CH$_2$=C(Cy)CH$_2$MgCl is used instead of 220 mL of a 2M-THF solution of CH$_2$=CHCH$_2$MgCl.

Example 3

Preparation of CF$_2$=CFCH$_2$CH(CH$_2$OCH$_2$OCH$_3$)CH$_2$CH=CH$_2$ 60 g of CF$_2$=CFCH$_2$CH(CH$_2$OCH$_2$OCH$_3$)CH$_2$CH=CH$_2$ (65-67° C./0.5 kPa) was obtained by carrying out the preparation in the same manner as in Example 1 except that in Example 1, 557 g of CF$_2$ClCFClI and 4.5 g of AIBN were used, 141.2 g of CH$_2$=CHCH$_2$OCH$_2$OCH$_3$ was used instead of 75.8 g of CH$_2$=CHCH$_2$C(CF$_3$)$_2$OCH$_2$OCH$_3$, and 1 L of dehydrated THF and 500 mL of a 2M-THF solution were used.

NMR spectra $^1$H-NMR (399.8 MHz, solvent: CDCl$_3$, standard: tetramethylsilane) δ (ppm): 1.78 (m, H), 1.96 (m, 1H), 2.18 (m, 2H), 2.37 (m, 2H), 3.44 (s, 3H), 3.61 (m, 2H), 4.95 (m, 2H), 5.10 (m, 2H), 0.79 (m, 1H).

$^{19}$F-NMR (376.2 MHz, solvent: CDCl$_3$, standard: CFCl$_3$) δ (ppm): −104.5 (dd, J=32.24, 85.96 Hz, 1F), −123.8 (ddt, J=4.29, 85.96, 113.9 Hz, 1F), −171.9 (ddt, J=23.6, 32.24, 113.9 Hz, 1F).

Preparation Example 1

Preparation of CF$_2$=CFCH$_2$CH(CH$_2$OH)CH$_2$CH=CH$_2$ 40 g of CF$_2$=CFCH$_2$CH(CH$_2$OCH$_2$OCH$_3$)CH$_2$CH=CH$_2$ obtained in Example 3 and 100 mL of methanol were put into a 300 mL glass reactor, and a catalytic amount of concentrated hydrochloric acid was added thereto, followed by heating at 60° C. for 19 hours. The reaction solution was cooled to room temperature, and 30 mL of water was added to carry out liquid separation. The organic layer was further washed with 50 mL of water and subjected to precision distillation to obtain 35.3 g of CF$_2$=CFCH$_2$CH(CH$_2$OH)CH$_2$CH=CH$_2$ (59-60° C./0.5 kPa).

NMR spectra $^1$H-NMR (399.8 MHz, solvent: CDCl$_3$, standard: tetramethylsilane) δ (ppm): 1.78 (m, 1H), 1.96 (m, 1H), 2.18 (m, 2H), 2.37 (m, 2H), 3.61 (m, 2H), 5.10 (m, 2H), 5.79 (m, 1H).

$^{19}$F-NMR (376.2 MHz, solvent: CDCl$_3$, standard: CFCl$_3$) δ (ppm): −104.5 (dd, J=32.24, 85.96 Hz, 1F), −123.8 (ddt, J=4.29, 85.96, 113.9 Hz, 1F), −171.9 (ddt, J=23.6, 32.24, 113.9 Hz, 1F).

Example 4

Preparation of CF$_2$=CFCH$_2$C(C(CH$_3$)(CF$_3$)OCH$_2$OCH$_3$)CH$_2$CH=CH$_2$ 25 g of CF$_2$=CFCH$_2$C(C(CH$_3$)(CF$_3$)OCH$_2$OCH$_3$)CH$_2$CH=CH$_2$ (45-47° C./0.15 kPa) was obtained by carrying out the preparation in the same manner as in Example 1 except that in Example 1, 385 g of CF$_2$ClCFClI and 28.1 g of AIBN were used, 178 g of CH$_2$=CHC(CH$_3$)(CF$_3$)OCH$_2$OCH$_3$ was used instead of 75.8 g of CH$_2$=CHCH$_2$C(CF$_3$)$_2$OCH$_2$OCH$_3$, and 1 L of dehydrated THF and 660 mL of a 2M-THF solution were used.

NMR spectra $^1$H-NMR (399.8 MHz, solvent: CDCl$_3$, standard: tetramethylsilane) δ (ppm): 1.38 (m, 3H), 2.19 (m, 4H), 2.44 (m, 1H), 2.67 (m, 1H), 3.44 (s, 3H), 4.95 (m, 2H), 5.12 (m, 2H) 5.82 (m, 1H).

$^{19}$F-NMR (376.2 MHz, solvent: CDCl$_3$, standard: CFCl$_3$) δ (ppm): −78.5 (d, J=62.3, 3F), −104.2 (dddd, J=4.29, 32.2, 49.4, 85.9 Hz, 1F), −123.0 (dd, J=38.7, 83.8 Hz, 1F), −173.1 (m, 1F).

Preparation Example 2

Preparation of CF$_2$=CFCH$_2$C(C(CH$_3$)(CF$_3$)OH)CH$_2$CH=CH$_2$ 10.7 g of CF$_2$=CFCH$_2$C(C(CH$_3$)(CF$_3$)OH)CH$_2$CH=CH$_2$ (40-42° C./0.15 kPa) was obtained by carrying out the preparation in the same manner as in Preparation Example 1 except that in Preparation Example 1, 25 g of CF$_2$=CFCH$_2$C(C(CH$_3$)(CF$_3$)OCH$_2$OCH$_3$)CH$_2$CH=CH$_2$ obtained in Example 3 was used instead of 40 g of CF$_2$=CFCH$_2$CH(CH$_2$OCH$_2$OCH$_3$)CH$_2$CH=CH$_2$, and 60 mL of methanol was used.

NMR spectra $^1$H-NMR (399.8 MHz, solvent: CDCl$_3$, standard: tetramethylsilane) δ (ppm): 1.38 (m, 3H), 2.19 (m, 4H), 2.44 (m, 1H), 2.67 (m, 1H), 5.12 (m, 2H), 5.82 (m, 1H).

$^{19}$F-NMR (376.2 MHz, solvent: CDCl$_3$, standard: CFCl$_3$) δ (ppm): −78.5 (d, J=62.3, 3F), −104.2 (dddd, J=4.29, 32.2, 49.4, 85.9 Hz, 1F), −123.0 (dd, J=38.7, 83.8 Hz, 1F), −173.1 (m, 1F).

Example 5

Preparation of CF$_2$=CFCH$_2$C(C(O)OC(CH$_3$)$_3$)CH$_2$CH=CH$_2$

Into a 200 mL glass reactor, 91.8 g of CF$_2$ClCFClI and 0.75 g of BPO were put and heated to 85° C. 30 g of CH$_2$=CHC(O)OC(CH$_3$)$_3$ was dropwise added thereto over a period of 0.5 hour. After completion of the dropwise addition, the mixture was stirred at 85° C. for 7 hours, and then distilled under reduced pressure to obtain 56 g of CF$_2$ClCFClCH$_2$CHI(C(O)OC(CH$_3$)$_3$) (80-85° C./0.2 KPa).

Into a 1 L glass reactor, 50 g of the above prepared CF$_2$ClCFClCH$_2$CHI(C(O)OC(CH$_3$)$_3$) and 360 mL of dehydrated THF were put and cooled to −75° C. 80 mL of a 1.6 M hexane solution of n-BuLi was dropwise added thereto over a period of 1.5 hours. After stirring at −75° C. for 1 hour, a solution prepared by diluting 22 g of allyl bromide with 50 mL of THF, was dropwise added thereto over a period of 1 hour. After further stirring for 3 hours, 200 mL of an aqueous saturated ammonium chloride solution was added thereto, and the temperature was raised to room temperature. The reaction solution was subjected to liquid separation, and the organic layer was concentrated by an evaporator and distilled under reduced pressure to obtain 22 g of CF$_2$ClCFClCH$_2$C(C(O)OC(CH$_3$)$_3$)CH$_2$CH=CH$_2$ (70-75° C./0.2 kPa). Into a 200 mL glass reactor, 22 g of zinc and 80 g of water were put and heated to 90° C. 22 g of the above prepared CF$_2$ClCFClCH$_2$C(C(O)OC(CH$_3$)$_3$)CH$_2$CH=CH$_2$ was dropwise added thereto and then stirred for 10 hours. The reaction solution was filtrated, and the organic is layer was distilled under reduced pressure to obtain 2.5 g of CF$_2$=CFCH$_2$C(C(O)OC(CH$_3$)$_3$)CH$_2$CH=CH$_2$ (50-55° C./0.8 kPa).

NMR spectra $^1$H-NMR (399.8 MHz, solvent: CDCl$_3$, standard: tetramethylsilane) δ (ppm): 1.37 (s, 9H), 2.39 (m, 5H), 5.02 (m, 2H), 5.65 (m, 1H)

$^{19}$F-NMR (376.2 MHz, solvent: CDCl$_3$, standard: CFCl$_3$) δ (ppm): −104.7 (dd, J=32.7, 85.0 Hz, 1F), −123.5 (m, 1F), −171.4 (m, 1F).

Example 6

Preparation of CF$_2$=CFCH$_2$C(C(O)O(AdM))CH$_2$CH=CH$_2$

CF$_2$=CFCH$_2$C(C(O)O(AdM))CH$_2$CH=CH$_2$ can be obtained by carrying out the preparation in the same manner as in Example 5 except that in Example 5, 55 g of CH$_2$=CHC(O)O(AdM) is used instead of 30 g of CH$_2$=CHC(O)OC(CH$_3$)$_3$.

Example 7

5.6 g of the monomer obtained in Example 1 was charged into a pressure resistant reactor made of glass and having an internal capacity of 30 mL. Then, 0.14 g of perfluorobenzyl peroxide was added as a polymerization initiator. The interior of the system was freezed-deaerated, and then the reactor was sealed, followed by polymerization for 18 hours in a constant temperature shaking bath (70° C.). After the polymerization, the reaction solution was dropped into hexane to reprecipitate the polymer, followed by vacuum is drying at 105° C. for 20 hours. As a result, 2.62 g of a non-crystalline polymer having a fluorinated cyclic structure in its main chain (hereinafter referred to as polymer 1A), was obtained. The molecular weight measured by GPC employing THF as a solvent and calculated as PSt, was such that the number average molecular weight (Mn) was 9,200, and the weight average molecular weight (Mw) was 17,100, and Mw/Mn=1.85. Tg measured by the differential scanning calorimetry (DSC) was 104° C., and the polymer was a white powder at room temperature. The polymer obtained was soluble in acetone, THF, ethyl acetate and methanol and was insoluble in R225, perfluoro(2-butyltetrahydrofuran) and perfluoro-n-octane.

By $^{19}$F-NMR and $^1$H-NMR, it was confirmed to be a cyclized polymer having the following monomer units of (d), (e) and (f).

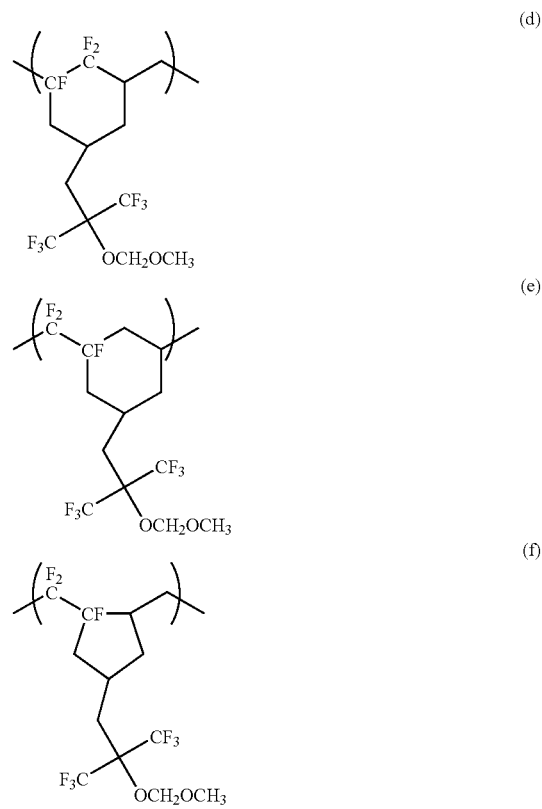

Example 8

1.25 g of the monomer obtained in Example 3, 5.01 g of the monomer obtained in Preparation Example 1 and 9.4 g of methyl acetate were charged into a pressure resistant reactor made of glass and having an internal capacity of 30 mL. Then, 0.23 g of perfluorobenzoyl peroxide was added as a polymerization initiator. The interior of the system was freeze-deaerated, and then the reactor was sealed, followed by polymerization for 18 hours in a constant temperature shaking bath (70° C.). After the polymerization, the reaction solution was dropped into hexane to reprecipitate the polymer, followed by vacuum drying at 106° C. for 16 hours. As a result, 1.05 g of a non-crystalline polymer having a fluorinated cyclic structure in its main chain (hereinafter referred to as polymer 2A), was obtained. The molecular weight measured by GPC employing THF as a solvent and calculated as PSt, was such that the number average molecular weight (Mn) was 5,100, and the weight average molecular weight (Mw) was 10,200, and Mw/Mn=2.02. Tg measured by the differential scanning calorimetry (DSC) was 98° C., and the polymer was a white powder at room temperature. The polymer obtained was soluble in acetone, THF and methanol and was insoluble in R225, perfluoro(2-butyltetrahydrofuran) and perfluoro-n-octane.

Example 9

2.34 g of the monomer obtained in Example 4, 9.36 g of the monomer obtained in Preparation Example 2 and 22.2 g of methyl acetate were charged into a pressure resistant reactor made of glass and having an internal capacity of 50 mL. Then, 0.408 g of IPP was added as a polymerization initiator. The interior of the system was freeze-deaerated, and then the reactor was sealed, followed by polymerization for 18 hours in a constant temperature shaking bath (40° C.). After the polymerization, the reaction solution was dropped into hexane to reprecipitate the polymer, followed by vacuum drying at 125° C. for 10 hours. As a result, 1.93 g of a non-crystalline polymer having a fluorinated cyclic structure in its main chain (hereinafter referred to as polymer 3A), was obtained. The molecular weight measured by GPC employing THF as a solvent and calculated as PSt, was such that the number average molecular weight (Mn) was 16,900, and the weight average molecular weight (Mw) was 34,700, and Mw/Mn=2.05. Tg measured by the differential scanning calorimetry (DSC) was 133° C., and the polymer was a white powder at room temperature. The polymer obtained was soluble in acetone, THF, ethyl acetate, methanol and 2-perfluorohexyl ethanol, and was insoluble in R225, perfluoro(2-butyltetrahydrofuran) and perfluoro-n-octane.

Example 10

2 g of the monomer obtained in Example 5 was charged into a glass tube having an inner diameter of 10 mm and a length of 300 mm. Then, 40 mg of perfluorobenzoyl peroxide was added as a polymerization initiator. The interior of the system was freeze-deaerated, and then the tube was sealed, followed by polymerization for 20 hours in a constant temperature shaking bath (70° C.). After the is polymerization, the reaction solution was dropped into methanol to reprecipitate the polymer, followed by vacuum drying at 130° C. for 20 hours. As a result, 1.36 g of a non-crystalline polymer having a fluorinated cyclic structure in its main chain (hereinafter referred to as polymer 4A), was obtained. The molecular weight measured by GPC employing THF as a solvent and calculated as PSt, was such that the number average molecular weight (Mn) was 23,700, and the weight average molecular weight (Mw) was 71,800, and Mw/Mn=3.03. Tg measured by the differential scanning calorimetry (DSC) was 90° C., and the polymer was a white powder at room temperature. The polymer obtained was soluble in acetone, THF, ethyl acetate, hexane, R225 and 2-perfluorohexyl ethanol, and was insoluble in methanol, perfluoro(2-butyltetrahydrofuran) and perfluoro-n-octane.

Example 11

5 g of the monomer obtained in Preparation Example 2 was charged into a pressure resistant reactor made of glass and having an internal capacity of 30 mL. Then, 0.14 g of perfluorobenzoyl peroxide was added as a polymerization initiator. The interior of the system was freeze-deaerated, and then the reactor was sealed, followed by polymerization for 18 hours in a constant temperature shaking bath (70° C.). After the polymerization, the reaction solution was dropped into hexane to reprecipitate the polymer, followed by vacuum drying at 105° C. for 20 hours. As a result, 2.1 g of a non-crystalline polymer having a fluorinated cyclic structure in its main chain, was obtained. By employing 2.1 g of the obtained polymer, a methanol solution of sodium hydroxide, and (1-adamantyl methyl)chloromethyl ether, it is possible to obtain a polymer having some hydroxyl groups of the polymer adamantylmethoxymethylated.

Example 12

30 g of $CF_2$=$CFCH_2CH(CH_2C(CF_3)_2OCH_2OCH_3)$ $CH_2CH$=$CH_2$ obtained in Example 1 and 100 mL of methanol were put into a 200 mL glass reactor, and a catalytic amount of concentrated hydrochloric acid was added thereto, followed by heating at 60° C. for 20 hours. The reaction solution was cooled to room temperature, and 30 mL of water was added to carry out liquid separation. The organic layer was further washed with 50 mL of water and subjected to precision distillation to obtain 25 g of $CF_2$=$CFCH_2CH$ $(CH_2C(CF_3)_2OH)CH_2CH$=$CH_2$. 12 g of the monomer obtained was charged into a pressure resistant reactor made of glass and having an internal capacity of 50 mL. Then, 0.45 g of perfluorobenzoyl peroxide was added as a polymerization initiator. The interior of the system was freeze-deaerated, and then the reactor was sealed, followed by polymerization for 18 hours in a constant temperature shaking bath (70° C.). After the polymerization, the reaction solution was dropped into hexane to reprecipitate the polymer, followed by vacuum drying at 100° C. for 22 hours to obtain 10.6 g of a polymer. 2 g of the obtained polymer, 1.25 g of a 7.7 wt % methanol solution of sodium hydroxide and 40 mL of methanol were put and stirred at 45° C. for 18 hours. The reaction solution was concentrated by an evaporator and then dissolved in 60 mL of dehydrated THF. Then, 0.472 g of $CH_2BrCOO(t-C_4H_9)$ was added thereto, and the mixture was stirred at room temperature for 66 hours and at 65° C. for 42 hours. The reaction solution was subjected to filtration through celite, and concentrated by an evaporator. The concentrated product was dissolved in R225 and washed with water, followed by liquid separation. The R225 layer was dropped into hexane to reprecipitate the polymer, followed by vacuum drying at 90° C. for 14 hours. As a result, 1.97 g of a non-crystalline polymer having a fluorinated cyclic structure in its main chain was obtained. By analyses of $^{19}$F-NMR and $^1$H-NMR, it was confirmed that 28 mol % of the hydroxyl group was blocked with —$CH_2COO(t-C_4H_9)$. Its molecular weight measured by GPC employing THF as a solvent and calculated as PSt, was such that the number average molecular weight (Mn) was 9,100, and the weight average molecular weight (Mw) was 16,300, and Mw/Mn=1.78. Tg measured by the differential scanning calorimetry (DSC) was 89° C., and the polymer was a white powder at room temperature. The polymer obtained was soluble in acetone, THF, methanol and R225.

Examples 13 to 16

1 g of each of polymers 1A to 4A prepared in Examples 7 to 10 and 0.05 g of trimethylsulfonium triflate were dissolved in 10 g of propylene glycol monomethyl ether acetate and filtered through a filter made of PTFE and filter having a pore diameter of 0.2 µm to produce a resist composition.

The above resist composition was spin-coated on a silicon substrate treated with hexamethyldisilazane, followed by heat treatment at 80° C. for 2 minutes to form a resist film having a thickness of 0.3 µm. In an exposure test apparatus flushed with nitrogen, the substrate having the above resist film formed, was placed, and a mask having a pattern drawn by chrome on a quartz plate, was put thereon in close contact therewith. KrF excimer laser beams were irradiated through the mask, whereupon, after exposure at 100° C. for 2 minutes, baking was carried out. The development was carried out at 23° C. for 1 minute with a tetramethyl ammonium hydroxide aqueous solution (2.38 mass %), followed by washing with pure water for 1 minute. The light transmittance of the resist film and the development test results are shown in Table 1.

TABLE 1

|  | Polymer | Transmittance of light of 157 nm (%) | Line and space width (1/1) (μm) |
|---|---|---|---|
| Ex. 13 | 1A | 55 | 0.18 |
| Ex. 14 | 2A | 45 | 0.19 |
| Ex. 15 | 3A | 50 | 0.19 |
| Ex. 16 | 4A | 30 | 0.20 |

INDUSTRIAL APPLICABILITY

The fluoropolymer of the present invention is applicable to ion exchange resins, ion exchange membranes, fuel cells, various cell materials, optical fibers, electronic members, transparent film materials, agricultural polyvinyl chloride films, adhesives, fiber materials, weather-resistant coating materials or the like, in addition to the use as a base polymer for photoresists.

The entire disclosures of Japanese Patent Application No. 2003-284156 filed on Jul. 31, 2003 and Japanese Patent Application No. 2004-088337 filed on Mar. 25, 2004 including specifications, claims and summaries are incorporated herein by reference in their entireties.

What is claimed is:

1. A fluorinated diene represented by the following formula (2):

$$CF_2=CFCH_2CH((CH_2)_aC(CF_3)_b(R^3)_cOR^4)-CH_2CH=CH_2 \quad (2)$$

wherein
  a is an integer of from 0 to 3,
  b and c are integers of from 0 to 2 satisfying b+c=2,
  $R^3$ is a hydrogen atom or a methyl group, and
  $R^4$ is an alkyl group having at most 5 carbon atoms which may have an etheric oxygen atom, an alkoxycarbonyl group having at most 6 carbon atoms or $CH_2R^5$ (wherein $R^5$ is an alkoxycarbonyl group having at most 6 carbon atoms).

2. The fluorinated diene according to claim 1, wherein b=2.
3. The fluorinated diene according to claim 1, wherein c=2.
4. The fluorinated diene according to claim 1, wherein a=0.
5. The fluorinated diene according to claim 1, wherein $R^3$ the hydrogen atom.
6. The fluorinated diene according to claim 1, wherein $R^3$ is the methyl group.
7. The fluorinated diene according to claim 1, wherein $R^4$ is the alkyl group having at most 5 carbon atoms.
8. The fluorinated diene according to claim 1, wherein $R^4$ is the alkoxycarbonyl group having at most 6 carbon atoms.
9. The fluorinated diene according to claim 1, wherein $R^4$ is the $CH_2R^5$ (wherein $R^5$ is an alkoxycarbonyl group having at most 6 carbon atoms).

* * * * *